United States Patent [19]

Bischoff

[11] Patent Number: 5,362,858
[45] Date of Patent: Nov. 8, 1994

[54] POLYETHYLENE GLYCOL-HIRUDIN CONJUGATES, PROCESS FOR PREPARING THEM AND THEIR USE FOR THE TREATMENT OF THROMBOSES

[75] Inventor: Rainer Bischoff, Illkirch-Graffenstaden, France

[73] Assignee: Transgene S.A., Strasbourg, France

[21] Appl. No.: 18,412

[22] Filed: Feb. 17, 1993

[30] Foreign Application Priority Data

Feb. 20, 1992 [FR] France ................. 92 01938

[51] Int. Cl.$^5$ ............... C07K 13/00; A61K 37/64; A61K 47/48
[52] U.S. Cl. ..................... 530/410; 530/345
[58] Field of Search ............. 530/345, 410, 350

[56] References Cited

U.S. PATENT DOCUMENTS

| | | | |
|---|---|---|---|
| 4,412,989 | 11/1983 | Iwashita et al. | 424/177 |
| 4,670,417 | 6/1987 | Iwasaki et al. | 514/6 |
| 4,766,106 | 8/1988 | Katre et al. | 514/12 |
| 4,847,325 | 7/1989 | Shadle et al. | 530/351 |
| 4,902,502 | 2/1990 | Nitecki et al. | 424/85.1 |
| 5,006,333 | 4/1991 | Saifer et al. | 424/78 |
| 5,066,590 | 11/1991 | Yabuki et al. | 435/180 |
| 5,169,627 | 12/1992 | Cunningham | 424/85.8 X |

FOREIGN PATENT DOCUMENTS

| | | |
|---|---|---|
| 0304311 | 2/1989 | European Pat. Off. . |
| 89/01033 | 2/1989 | WIPO . |
| 91/08229 | 6/1991 | WIPO . |
| 9215610 | 9/1992 | WIPO . |

OTHER PUBLICATIONS

Freiser, Hajestam et al., Bio Chromatography, vol. 2(4), pp. 186-189, (1987).

*Primary Examiner*—Michael G. Wityshyn
*Assistant Examiner*—C. Sayala
*Attorney, Agent, or Firm*—Burns, Doane, Swecker & Mathis

[57] ABSTRACT

The present invention relates to a process for preparing a polyethylene glycol (or derivatives)-hirudin conjugate. It also relates to the polyethylene glycol (or derivatives)-hirudin conjugate obtained and its use as medicinal product for the treatment of thromboses.

17 Claims, 4 Drawing Sheets

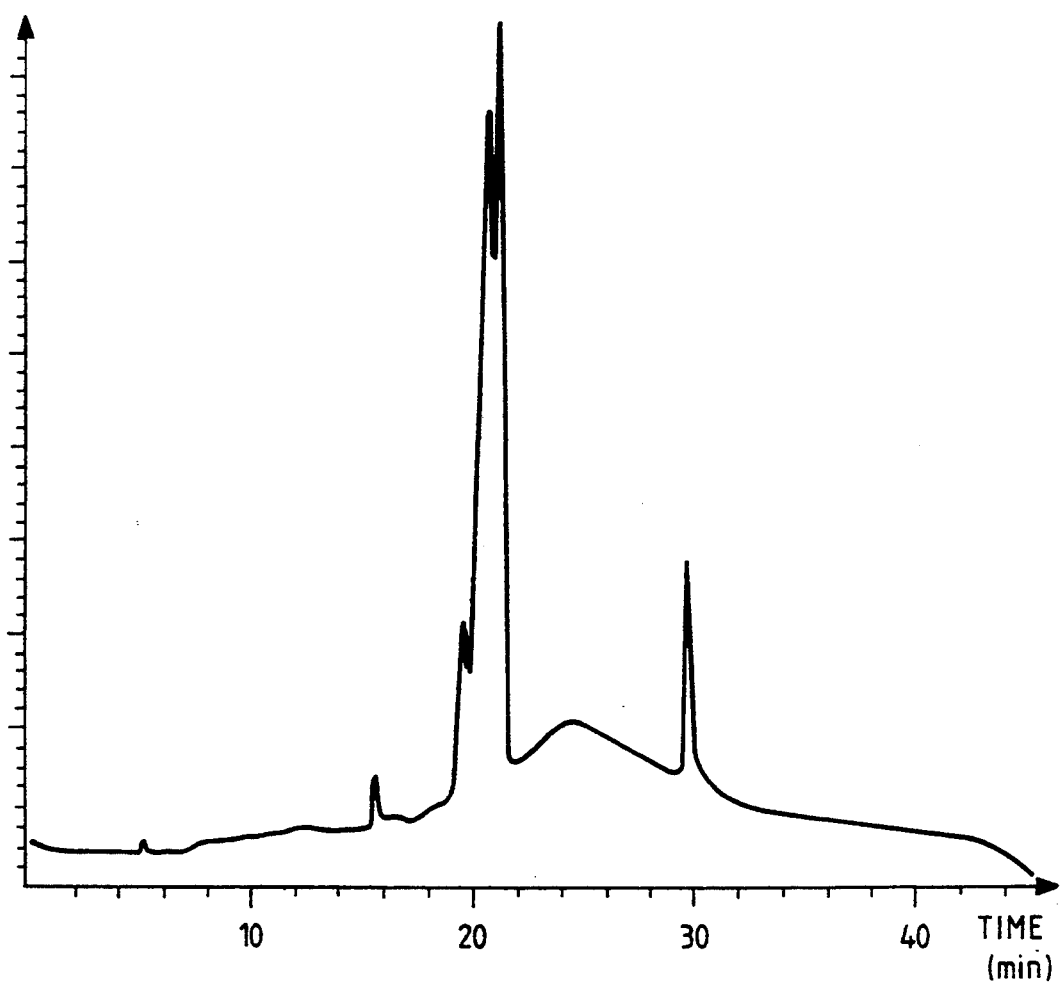
FIG_1

FIG_2
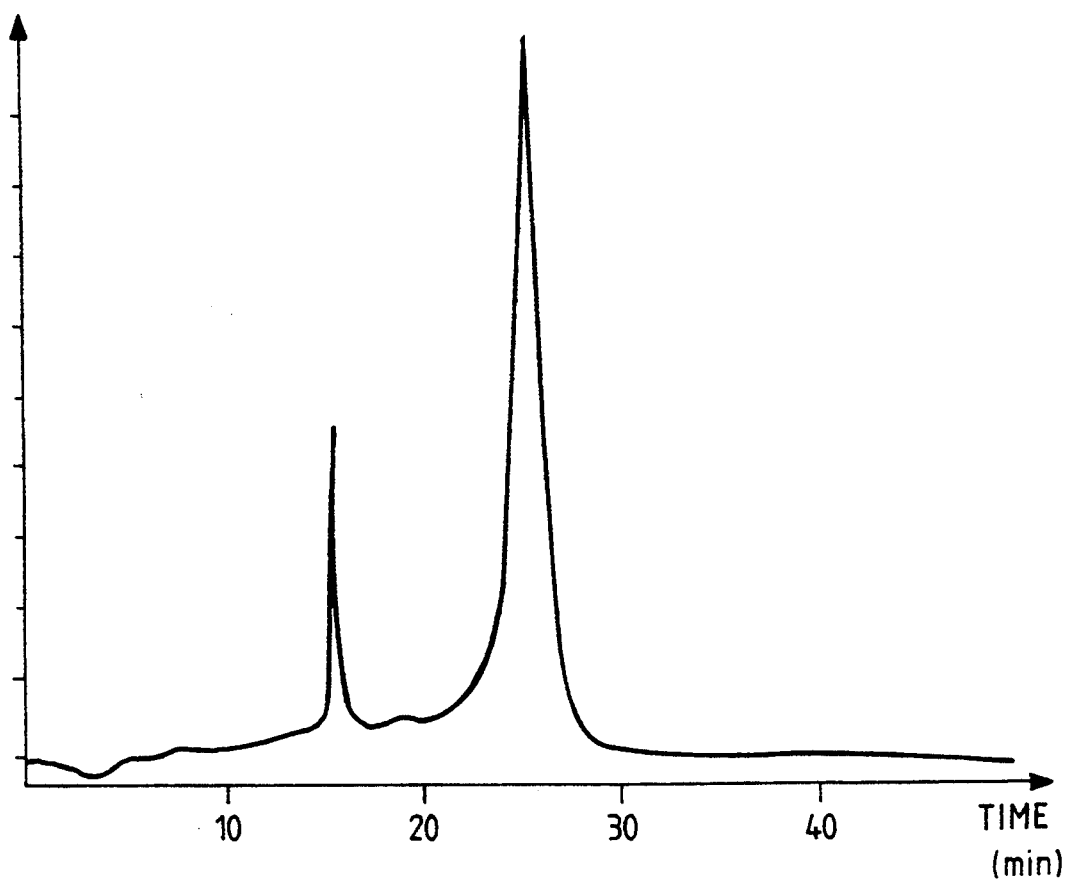

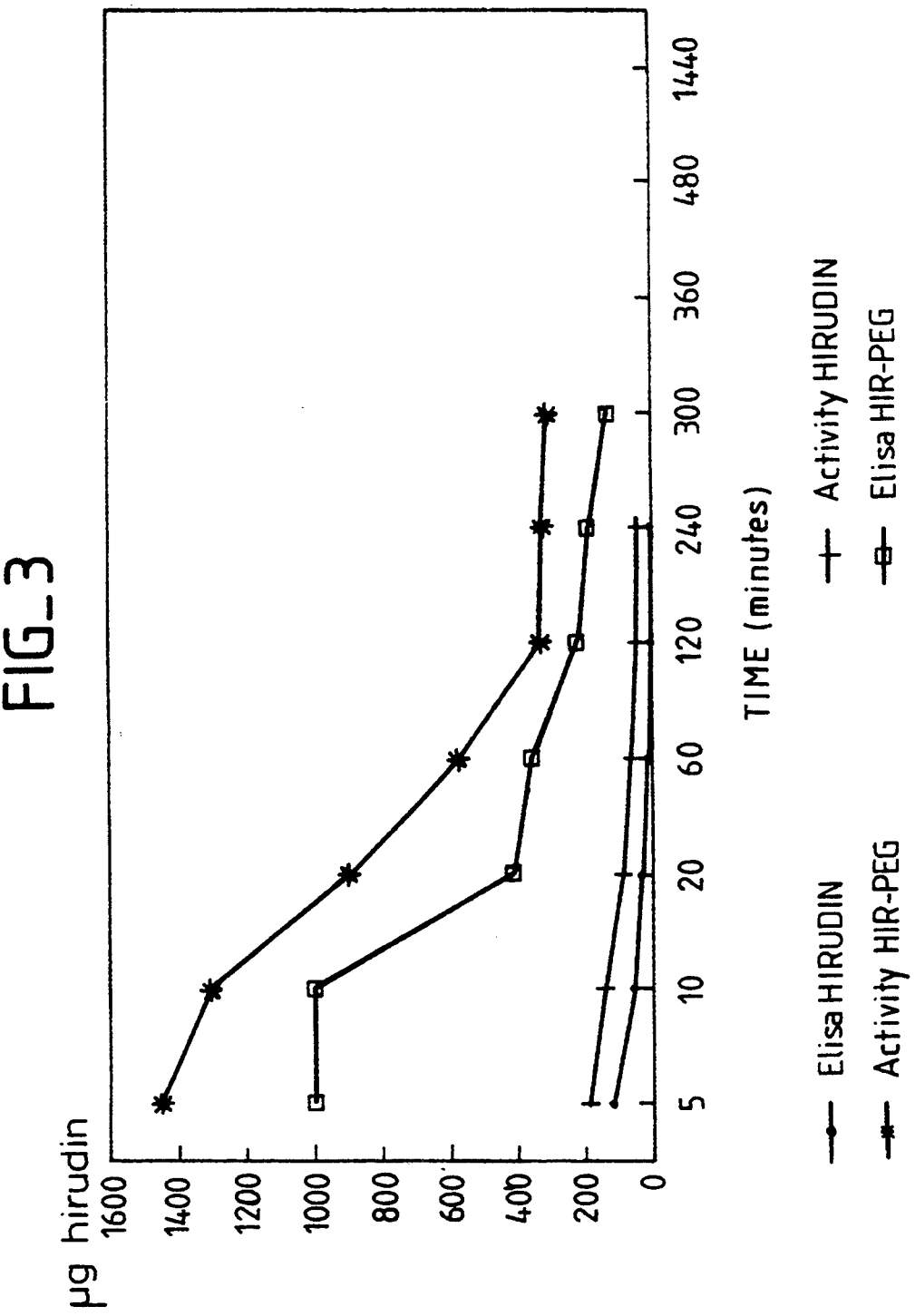

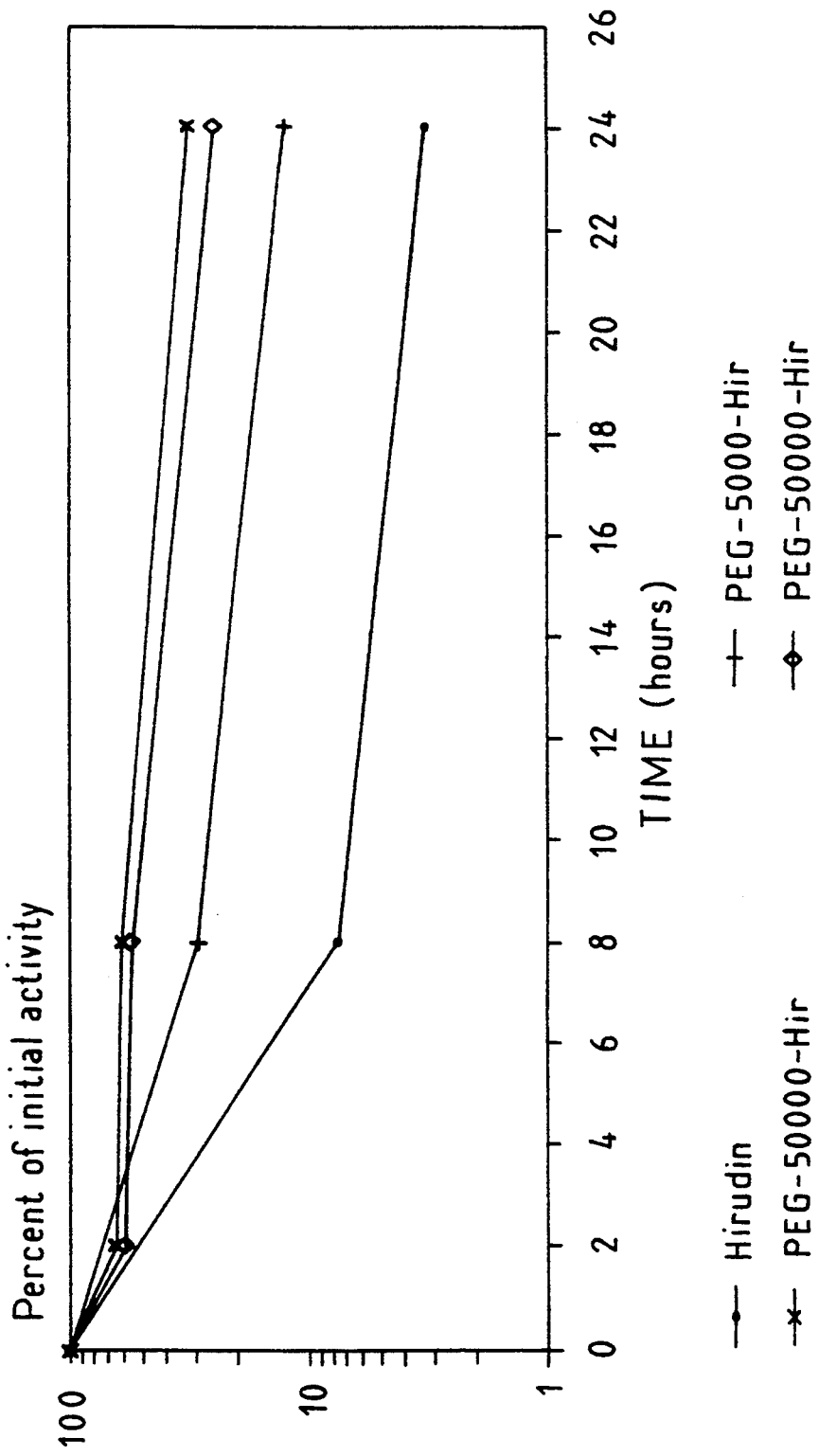
FIG_4

POLYETHYLENE GLYCOL-HIRUDIN CONJUGATES, PROCESS FOR PREPARING THEM AND THEIR USE FOR THE TREATMENT OF THROMBOSES

The present invention relates to a process for preparing a polyethylene glycol (or derivatives)-peptide conjugate, hereinafter PEG-peptide, and in particular a polyethylene glycol (or derivatives)-hirudin (PEGhirudin) conjugate.

Compounds such as polyethylene glycol and its derivatives, hereinafter PEG, or Dextran are known not to be immunogenic in man and their use in combination with proteins intended for pharmacological use has already been proposed in order to prolong the half-life of these proteins in vivo.

Thus, a peptide such as hirudin, of which the principle source is found in the salivary glands of medicinal leeches in the form of a mixture of peptides containing 65 and 66 amino acids, known for its very specific and very effective thrombin inhibiting properties, is very rapidly removed from the bloodstream. Its half-life period is about 1 h. It is therefore very advantageous to prolong the in vivo half-life of hirudin, in particular for its use in the prophylaxis of thromboses.

To increase the half-life of hirudin in vivo, a Dextran-hirudin conjugate was produced by P. Crause (EP-A-0,345,616). Although the half-life of Dextran-hirudin is increased in vivo in rats compared with the half-life of free himdin, the yield of the process for coupling hirudin with Dextran is very low since a loss of more than 70% of the activity of the conjugated hirudin is observed.

PEG-peptide coupling is also known and is generally obtained by means of a covalent bond.

The process for coupling PEG with a peptide comprises the two main steps of activation of PEG, and of coupling of the activated PEG with the peptide.

The first activation step is generally limiting for the final yield of conjugate obtained.

Indeed, the prior art proposes processes for activating PEG which require a step for purifying and recovering the activated PEG, which is carried out with low yields.

Thus, Beauchamp et al. (Analytical Biochemistry 1983, 131, 25–33) describe a process for activating PEG by reaction with carbonyldiimidazole in dioxane, which comprises a step for purifying the activated PEG by extensive dialysis against water and freeze-drying.

Being extensive, this dialysis poses problems for its application on an industrial scale. Moreover, the activated PEG is inactivated in an aqueous medium, which causes a decrease in the yield of the activation reaction due to the dialysis step.

The present invention therefore relates to a process for preparing a PEG-peptide conjugate which is simple and rapid to use and which is applicable on an industrial scale. The present invention advantageously relates to a process for preparing a PEG-hirudin conjugate, of which at least 80% of the hirudin is coupled with PEG and the conjugates obtained have an activity close to 100% compared with the starting hirudin.

The process according to the present invention comprises the known steps of activating the PEG in an appropriate anhydrous solvent, of recovering the PEG and its reaction with a peptide.

PEG, or polyethylene glycol and its derivatives, is mainly understood to mean polyethylene glycol and the $C_1$-$C_6$ lower aliphatic monoethers of polyethylene glycol, also the aromatic monoethers or the monoesters of polyethylene glycol, as well as the polyglycolated derivatives comprising at least 90% of ethylene glycol units relative to the total number of monomeric units.

It was found, surprisingly, that PEG activated by means of an activating agent chosen from carbonyldiimidazole, N-hydroxysuccinimide and 2,3,5-trichloroformate could be purified simply by precipitation from the activation mixture by means of a hydrophobic organic solvent and remain active for the subsequent step of condensation with a peptide.

The hydrophobic organic solvent is chosen from apolar or barely polar aprotic solvents, among which are aliphatic ethers and hydrocarbons.

Advantageously, this hydrophobic organic solvent is selected from ethyl ether, pentane, hexane or heptane, preferably ethyl ether.

The activated PEG is then recovered by filtration and then freeze-dried.

The PEG activation reaction is carried out in an appropriate anhydrous solvent, preferably in a polar aprotic solvent.

This appropriate anhydrous solvent is generally chosen from dioxane, dimethylformamide, acetonitrile, dimethyl sulphoxide or tetrahydrofuran.

Preferably, PEG is activated by means of carbonyldiimidizole as activating agent.

The molar ratio between the activating agent and the PEG, during activation of the latter, is between 5 and 50, preferably between 10 and 20.

The PEG used in the process according to the present invention has a molecular weight of between 2,000 and 100,000, advantageously of between 2,000 and 50,000, and is chosen from polyethylene glycol and $C_1$-$C_6$ aliphatic monoesters of polyethylene glycol.

The activated PEG obtained by reaction with carboxydiimide may thus be represented by the following general formula I:

$$R-(O(CH_2)_2)_n-O-\underset{\underset{O}{\|}}{C}-N\overbrace{\phantom{xx}}^{N} \qquad (I)$$

it being possible for R to be especially either a hydrogen atom, a $C_1$-$C_6$ alkyl radical or a carboxyimidazole group, n being between about 45 and about 2,400. The coupling with the peptide is carried out at a slightly alkaline pH by substituting the imidazole ring by a free amine functional group of the peptide.

The conjugate obtained may thus be represented by the following general formula II:

$$R-(O(CH_2)_2)_n-O-\underset{\underset{O}{\|}}{C}-NH\text{-Peptide} \qquad (II)$$

R and n being defined as above.

In a particularly advantageous manner, the process according to the present invention is used for the preparation of a PEG-hirudin conjugate.

Hirudin is understood to mean the natural hirudin extracted from the salivary glands of medicinal leeches, its natural variants some of which have been designated by HV1, HV2 and HV3 as well as the variants and analogs produced by genetic engineering and which conserve their anti-thrombotic activity.

The preparation of these peptides by genetic engineering has been described, in particular, in patent applications EP-A-0,158,564, EP-A-0,200,655, EP-A-0,273,800 and EP-A-0,332,529.

Hirudin contains several lysine groups in its peptide sequence. The activated PEG is therefore capable of becoming attached, in a random manner, to the N terminal functional group of the peptide or any one of the amine functional groups of the different lysine groups.

Yet, unexpectedly, the activated PEG does not become attached to the N-terminal amine of hirudin, which makes it possible to obtain a conjugate with an antithrombotic activity close to that of the peptide alone.

Consequently, the present invention also relates to a process for preparing a PEG-hirudin conjugate, comprising:

a) the activation of PEG by reaction with carbonyldiimidazole in an appropriate anhydrous solvent,
b) the recovery of the activated PEG by precipitation by means of a hydrophobic solvent,
c) the condensation of the activated PEG with hirudin or its variants, in a slightly alkaline medium, and
d) the purification of the conjugate obtained.

Steps a), b) and c) of the preparation of the activated PEG and its condensation with the peptide are carried out under the operating conditions described above.

Step d) for the purification of the PEG-hirudin conjugate obtained is generally carried out by chromatography in two steps:

d1) by anion-exchange chromatography to remove the excess PEG which may not have reacted, followed by a
d2) reversed-phase chromatography to separate the conjugate obtained from the residual free hirudin.

The anion-exchange resin employed for d1) is advantageously a D-Sepharose or Q-Sepharose, and the reversed phase in d2) an RP300 or RP8 phase.

The yield of conjugated hirudin obtained is greater than 60%.

Advantageously, the process according to the present invention is employed on the hirudin variant HV2-Lys47.

Finally, the present invention also relates to the PEG-hirudin conjugates obtained by the process described above and their use as therapeutic agent intended for the treatment of thromboses.

The examples below, with reference to the figures in the appendix, are intended to illustrate the present invention for the preparation of activated PEG, that of a PEG-hirudin conjugate and the anti-thrombotic activity of the conjugate obtained.

BRIEF DESCRIPTION OF THE DRAWINGS

FIG. 1 represents a chromatogram obtained after chromatography of PEG monomethyl ether 5,000-rHV2-Lys47 (MPEG 5,000-rHV2-Lys47) on the RP300 column. Elution of the proteins is monitored over time by measuring the optical density (OD) at 215 nm.

FIG. 2 represents a chromatogram obtained after chromatography of PEG 50,000-rHV2-Lys47 on the Lichrosphere RP8 column. Elution of the proteins is monitored over time by measuring the OD at 280 nm.

FIG. 3 represents, in the form of a graph, the plasma concentration of free or conjugated rHV2-Lys47 as a function of time, during the experiment over a short period described in Example 7c.

FIG. 4 represents, in the form of a graph, the percentage activity of free or conjugated rHV2-Lys47 as a function of time, during the experiment over a long period described in Example 7c.

EXAMPLE 1 preparation of activated PEG monomethyl ether (5,000) (MPEG 5,000)

All the reaction for activating MPEG 5,000 is carried out in an anhydrous medium. It is therefore necessary, in a first instance, to remove any trace of water which may be present in the constituents of the reaction medium. Stocks of MPEG 5,000 (Merck) and N,N'-carbonyldiimidazole (CDI) (Aldrich) are preserved in a desiccator containing silica gel in order to capture the water. A 5 A molecular sieve (Prolabo) is dried in an oven heated to 400° C., then the temperature is allowed to fall to 50° C. and the molecular sieve is added to 500 ml of dioxane (SDS) in order to capture the water present in the solvent.

25 g (about 4 mmol) of MPEG are added to 8.1 g (about 50 mmol) of CDI and the mixture is freeze-dried for at least 2 h. The dried powder is taken up in 50 ml of dioxane and the reaction for activating MPEG 5,000 with CDI (FIG. 1) is carried out for 2 h at 37° C., with stirring. As the molecules of MPEG 5,000 have only one free hydroxyl group, they have only one possible activation site.

The recovery of activated MPEG 5,000 is carried out by precipitation with ether. When the temperature of the reaction medium has decreased to 20° C. or less, 2 volumes of ether are added, with stirring, which causes the MPEG 5,000 to precipitate instantly while the excess CDI and the imidazole released during the reaction remain in solution. The solution is then filtered on a Whatmann 44 filter, the filter is washed with ether and the precipitate of freeze-dried activated MPEG 5,000 is taken up in 50 ml of dioxane and reprecipitated with ether as described above. After filtration, the activated MPEG 5,000 is freeze-dried overnight and then it is preserved in a desiccator containing silica gel so as to protect it from water.

EXAMPLE 2

Preparation of activated PEG 50,000.

All the reaction for activating PEG 50,000 is carried out in an anhydrous medium. To remove all traces of water, the PEG 50,000, CDI and dioxane are treated as described in Example 1.

19,2 g (about 384 μmol) of PEG 50,000 are added to 1 g (about 6 mmol) of CDI and the mixture is freeze-dried for at least 2 h. The dried powder is then taken up in 50 ml of dioxane and the reaction for activating PEG 50,000 with CDI is carried out for 15 h a 60° C., with stirring. The molecules of PEG 50,000 have two free hydroxyl groups; there are therefore two potential activation sites per molecule of PEG 50,000.

The activated PEG 50,000 is recovered by precipitation with ether as described in Example 1. 18.6 g of activated PEG 50,000 are recovered.

EXAMPLE 3

Coupling of the activated MPEG (5,000) with hirudin rEV2-Lys47.

A. Conjugation of MPEG 5,000 with rV2-Lys47

3 g (about 0.5 mmol) of activated MPEG 5,000 of Example 1 are mixed with 15 mg (about 2 μmol) of rHV2Lys 47 in 25 ml of 100 mM borate buffer at pH 8.4. The reaction medium is left for 12 h at 4° C., with stirring. As the activated MPEG 5,000 is rapidly inactivated on contact with water, 3 g of activated MPEG 5,000 are added to the reaction medium about every 12 h, 4 times in succession. After the fourth addition of activated MPEG 5,000, the reaction medium is again left for 48 h at 4° C.

B. Purification of the MPEG 5,000-rHV2-Lys 47 conjugate

The purification of the MPEG 5,000-rHV2-Lys47 conjugate is carried out in 2 steps:

i) an anion-exchange chromatography makes it possible to remove the excess MPEG 5,000 which is not retained whilst the MPEG 5,000-rHV2-Lys47 and free rHV2-Lys47 are adsorbed on the column.

ii) a reversed-phase chromatography makes it possible to separate residual free rHV2-Lys47 from MPEG 5,000-rHV2-Lys47.

1. Artion-exchange chromatography on Q-Spharose.

10 ml of phase are poured into a Biorad column 14 mm in diameter, and eguilibrated with 50 ml of equilibration buffer : 10 mM borate at a flow rate of 1 ml/min. The entire chromatography is performed at a flow rate of 1 ml/min. The reaction medium, containing the MPEG 5,000-rHV2-Lys47 obtained in B., is diluted 1/10 with water so as to have a solution containing 10 mM borate. A sample of about 250 ml is obtained which is loaded on the Q-Sepharose column. The column is washed with 50 ml of eguilibration buffer, then the elution is carried out using 10 ml of 10 mM borate buffer pH 8.5, 1M NaCl, and the column is reequilibrated in equilibration buffer. A 20-ml sample, containing the free rHV2-Lys47 and the MPEG 5,000-rHV2-Lys47, is recovered which corresponds to the 10 ml for the elution plus the first 10 ml for the reequilibration of the cole.

2. Chromatography on the reversed phase RP300.

The entire chromatography is performed at a flow rate of 1 ml/min. An Aquapore RP300 column 95 mm diameter and 250 mm long (Applied Biosystems) and a Hewlett Packard HP 1090 HPLC are used.

The pH of the sample obtained in 1, containing free rHV2-Lys47 and MPEG 5,000-rHV2-Lys47, is decreased to 2 with 10 mM TFA equilibration buffer in water, which increases the final volume to 35 ml. 5 ml of sample are injected into the R300 column and then the column is washed with equilibration buffer so as to remove the salts present in the sample. The elution is then performed using a 40 min gradient from 0 to 100% acetonitrile, containing 10 mM TFA, and then the column is washed with 10 to 20 ml of equilibration buffer. Elution of the proteins is monitored by measuring the OD at 215 nm. The procedure is carried out 7 times so as to chromatograph the 35 ml of sample. A chromatogram is presented in FIG. 1. Two fractions are recovered:

fraction 1 corresponds to the peak whose retention time is 15 min and contains free rHV2-Lys47, fraction 2 corresponds to the peaks whose retention times are between 19 and 22 min, and contains MPEG 5,000-rHV2-Lys47.

Comparison of the elution peaks for rHV2-Lys47 (fraction 1) and M/PEG 5,000-rHV2-Lys47 indicates that more than 95% of rHV2-Lys47 is coupled with MPEG 5,000.

The 7 fractions 1, containing free rHV2-Lys47, obtained during the 7 chromatographies, are mixed, then freeze-dried overnight, and taken up in PBS buffer (see table). The procedure is carried out in the same manner for the 7 fractions 2 containing MPEG 5,000-rHV2-Lys47.

The N-terminal sequence of the conjugate obtained was able to be determined normally, which indicates that activated MPEG 5,000 does not become attached to the terminal amine functional group of rHV2-Lys47.

EXAMPLE 4

Coupling of activated PEG 50,000 with hirudin rHV2-Lys47

A. Conjugation of PEG 50,000 with rHV2-Lys47.

2 g. (about 40 μmol) of activated PEG 50,000 of Example 2 g (about 40 mmol) of activated PEG 50,000 of Example 2 are mixed with 2 mg (about 280 nmol) of rHV2-Lys 47 in 5 ml of 100 mM borate buffer at pH 8.4. The reaction medium is left for 24 h at 4° C., with stirring. As the activated PEG 50,000 is rapidly inactivated on contact with water, 2 g of activated PEG 50,000, contained in 5 ml of 100 mM borate buffer, are added to the reaction medium every 24 h, 4 times in succession. 36 ml of a solution of PEG 50,000-rHV2-Lys47 are recovered.

B. Purification of the PEG 50,000-rF2-L-s47 conjugate

As with MPEG 5,000-rHV2-Lys47, purification of the PEG 50,000-rHV2-Lys47 conjugate is carried out in 2 steps:

i) an anion-exchange chromatography and, ii) a reversed-phase chromatography.

1. Anion-exchange chromatography on Q-Sepharose.

10 ml of phase are poured into a Biorad column 14 mm in diameter, and equilibrated with 50 ml of equilibration buffer: 10 mM borate, pH 8.5, at a flow rate of 1 ml/min. The entire chromatography is performed at a flow rate of 1 ml/min. The reaction medium, containing the PEG 50,000-rHV2-Lys47 obtained in B., is diluted 1/10 with water so as to have a solution containing 10 mM borate. A sample of about 360 ml is obtained which is chromatographed on the Q-Sepharose column in 3 portions. 120 ml of samples are loaded onto the Q-Sepharose columnwhich is then washed with 50 ml of equilibration buffer, then the elution is carried out with 10 ml of 10 mM borate buffer pH 8.5, 1 M NaCl, and the column is reequilibrated in equilibration buffer. A 40-ml sample, containing free rHV2-Lys47 and PEG 50,000rHV 2-Lys47, is recovered which corresponds to the 10 ml for the elution plus the first 30 ml for reequilibration of the column.

2. Chromatography on reversed-phase Lichrosphere RP8

The entire chromatography is performed at a flow rate of 1 ml/min. A 5 μ Lichrosphere RP8 column (Hewlett Packard) 4 mm in diameter and 125 mm long and a Hewlett Packard HP 1090 HPLC are used.

The pH of the sample obtained in 1, containing free rHV2-Lys47 and PEG 50,000-rHV2-Lys47, is decreased to 1.5 with 200 μl of pure TFA. The column is equilibrated in 10 mM TFA equilibration buffer in water. 20 ml of sample are injected into the RP8 column, then the column is washed with equilibration buffer so as to remove the salts present in the sample. The elution is then carried out using a 40 min gradient from 0 to 100% acetonitrile containing 10 mM TFA, and the column is washed with 10 to 20 ml of equilibration buffer. Elution of the proteins is monitored by measuring the OD at 215 nm. The procedure is carried out twice so as to chromatograph the 40 ml of sample. A chromatogram is represented in FIG. 2. Two fractions are recovered:

fraction 1 corresponds to the peak whose retention time is 15 min and contains free rHV2-Lys47, fraction 2 corresponds to the peaks whose retention times are between 20 and 30 min and contains PEG 50,000-rHV2-Lys47.

Comparison of the elution peaks for rHV2-Lys47 (fraction 1) and PEG 50,000-rHV2-Lys47 (fraction 2) indicates that more than 70% of rHV2-Lys47 is coupled with PEG 50,000.

The 7 fractions 1, containing free rHV2-Lys47, obtained during the 2 chromatographies, are mixed, then freeze-dried overnight, and taken up in PBS buffer. The procedure is carried out in the same manner for the 2 fractions 2 containing PEG 50,000-rHV2-Lys47.

EXAMPLE 5 quantification and activity of the conjugates obtained

Quantification of the conjugates obtained in Examples 3 and 4 was carried out using 3 different methods:

- reversed-phase analytical chromatography (analytical HPLC),
- test for anti-thrombin activity, and
- analysis of the amino acids a) Analytical chromatography A 5 μ Lichrosphere RP8 column (Hewlett Packard) 4 mm in diameter and 125 nun long and a Hewlett Packard HP 1090 HPLC are used. The flow rate is 1 ml/min during the entire chromatography.

The RP8 Lichrosphere column is equilibrated in an equilibration buffer: 30% acetonitrile, 10mMTFA and 70% water. About 25 μg of PEG-rHV2-Lys47, contained in 500 μ of PBS, are injected into the column, and after washing the column with equilibration buffer, the elution is carried out using a 40 min gradient from 30 to 65% acetonitrile in water containing 10 mMTFA, and then the column is reequilibrated in the equilibration buffer. Elution of proteins is monitored by measuring the OD at 215 nm, which is characteristic of proteins. The area of the elution peaks present on the chromatogram is proportional to the quantity of protein injected into the column. Chromatography of a known quantity of rHV2-Lys47, under the same conditions as those described above, makes it possible to correlate the area of the elution peak with the quantity of rHV2-Lys47 injected.

b) Anti-thrombotic activity

The activity of hirudin is assayed using a test for thrombin inhibition. The substrate used in this test is ChromozymepL(tosyl-glycyl-prolyl-lysine-4-nitranilide acetate) which is cleaved by thrombin and releases a chromophore which absorbs light at 410 nm.

The rate of formation of the chromophore depends on the quantity of active thrombin present in the reaction medium. In the presence of hirudin, thrombin is inhibited and the rate of formation of the chromophore is slower.

Products used for the activity test:

- rHV2-Lys47:2.5 mg/ml, preserved on ice
- thrombin: 3.3 μg/ml (1U/ml), in kinetics buffer, preserved on ice
- Chromozym® PL (Boehringer): 6.66 mg/ml, preserved at room temperature
- kinetics buffer: 50 mMTris-HCl 0.1 M NaCl 0.1% PEG 6,000 pH 7.9 thermostatted at 37° C.

The reaction is monitored at 410 nm in a spectro-photometer thermostated at 37° C. by means of a water bath. Between 0 and 100 μl of hirudin are mixed, in a 1-ml plastic spectrometer cuvette, with 50 μl of thrombin in the kinetics buffer so as to have a final volume of 980 μl. The cuvettes are preincubated for 3 min at 37° C. so that hirudin can become attached to the thrombin. 20 μl of Chromozym® are added to each cuvette and, after stirring, the OD is read at 410 nm every minute for minutes. The result is given in OD/min.

The specific activity of rHV2-Lys47 being known (15,000 ATU/mg), assaying the activity of the conjugate allows the latter to be quantified.

c) Analysis of the amino acids

The amino acid analysis is carried out in a conventional manner. The conjugate is hydrolysed using 6N HCl fumes, and then the amino acids are conjugated with phenyl isothiocyanate (PITC) in 5% n-heptane, which absorbs light at 254 nm. The amino acid conjugates are injected into a $C_{18}$ reversed-phase column and are then eluted using a gradient which makes it possible separate the various conjugates. Conjugation of the amino acids with PITC and the chromatography are performed in an Applied Biosystems 130A amino acid analyzer. The retention time on the reversed-phase column is specific for each amino acid conjugate. A standard solution of amino acid conjugates makes it possible to define these retention times and to quantify the amino acids present in the hydrolysate of the rHV2-Lys47 conjugate. Knowing the amino acid composition of rHV2-Lys47, the exact quantity of rHV2-Lys47 thus analysed can be determined.

The results obtained for the conjugates of Examples 3 and 4 are given in Table I below.

TABLE I

| Example | Volume ml | Quantification (in μg) analytical HPLC | activity test | amino acid analysis |
|---|---|---|---|---|
| 3 | 17 | 8200 | 8000 | 9194 |
| 4 | 1.7 | 1688 | 1070 | 1208.8 |

The fact thqt for these two examples, the activity tests give quantification results which are similar to those obtained by analytical HPLC or amino acid analysis clearly shows that nearly 100% of the PEG-hirudin conjugates obtained are active (between 85 and 98% for Example 3 and between 63 and 88% for Example 4).

These results make it possible to envisage their subsequent use as an anti-thrombotic agent without the need for further purification of the active conjugates.

EXAMPLE 6

Measurement of the inhibition constant for hiradin rHV2-Lys47 and its two conjugates with MPEG 5,000 and PEG 50,000.

Analysis of the inhibition constant is carried out according to the method described by R. S. Stone and J. Hofsteenge in Biochemistry, 1986, 25, pages 4628, and Biochemistry, 1991, 4, pages 295–300.

Hirudin inhibits thrombin according to a competitive type mechanism. The inhibition constant can therefore be calculated as follows:

$$Ki = \frac{K_i'}{1 + S/K_M}, \text{ with}$$

$K_i$ = inhibition constant,
$K_i'$ = apparent inhibition constant,
$K_M$ = 3.63 μM = Michaelis constant, and
S = substrate concentration.
$K_i'$, and S can be measured.

The results obtained are given in Table II below.

TABLE II

| Inhibitor | $K_i'$ (pM) | | $K_i$(pM) |
|---|---|---|---|
| rHV2-Lys47 | 29.30 | 1.77 | 1.03 |
| MPEG 5000-rHV2-Lys47 | 28.78 | 1.43 | 1 |
| PEG 50,000-rHV2-Lys47 | 34.12 | 1.04 | 1.19 |

The binding of MPEG 5,000 or PEG 50,000 does not affect the inhibition constant for the rHV2-Lys47thrombin complex. These results show that the PEG-hirudin conjugates are thrombin inhibitors which are as effective as free hirudin.

EXAMPLE 7

Pharmacokinetic tests in vivo

To evaluate the half-life of free rHV2-Lys47 and PEG-rHV2-Lys47 in rat plasma, 2 types of experiments were carried out:

experiment of a short period: it lasts for a maximum of only 5 to 6 h during which the rats are anaesthetised;

experiment over a long period: it lasts for 48 h and the rats are conscious during the entire duration of the experiment.

For the experiments, 300-g Sprague Dawley strain of rats are used. 5 days before the beginning of the experiments, the rats are separated in individual cages, they are acclimatised to a day-night cycle of 13 h, and they have water and feed ad libitum.

Blood samples are collected in plastic tubes containing a 3.2% sodium citrate solution, in a ratio of 1 volume to 4 volumes of blood.

Plasma is prepared from the blood within 10 min following collection, by centrifugation at 4,000 g for 5 min at room temperature. The plasma samples are stored at −80 ° C. The conjugate employed is MPEG 5,000-rHV2Lys-47, for the experiment over a short period, and MPEG 5,000-rHV2-Lys47 as well as PEG 50,000-rHV2-Lys47 for the experiment over a long period.

a) Experiment over a short period

Each experiment is carried out in parallel on 2 rats. On the day of the experiment, the rats are anaesthetised by administration of sodium pentobarbital (50 mg/kg) intraperitoneally. A catheter is placed in the right Jugular vein in order to administer 500 μg of rHV2-Lys47 in free (control) or conjugated form. A second catheter is placed in the left carotid in order to collect the blood samples.

Blood samples are collected before injection of rHV2-Lys47 or PEG-rHV2-Lys47 (t0), and at 5 min, 10 min, 20 rain, 1 h, 1 h, 4 h, 5 h and 6 h after the injection.

b) Experiment over a long period

Each experiment is carried out in parallel on 2 rats. On the day of the experiment, 500 μg of rHV2-Lys47, in free (control) or conjugated form, are administered into the rats' tail vein. The blood samples are collected under a mild anaesthesia with ether, from the rats' tail vein, before the injection of rHV2-Lys47 or PEG-rHV2Lys47 (t0), and at 5 min, 8 h and 24 h after the injection. Except for these periods, the rats are conscious during the entire duration of the experiment.

c) Analysis of the plasma samples

The quantity of rHV2-Lys47 in free (control) or conjugated form is determined by an ELISA test and by an activity test in the experiments over a short period. A calibration series is prepared with a properly quantified solution of rHV2-Lys47 or MPEG 5,000-HV2-Lys47, diluted in plasma collected at t0, so as to be under conditions similar to those for the samples collected. The plasma samples are diluted in kinetics buffer so that the concentration of rHV2-Lys47 falls within the calibration series. In the experiments over a long period, the quantity of rHV2-Lys47, in free form or in conjugated form (with MPEG 5,000 and PEG 50,000), is determined by an anti-thrombin activity test. The results of these analyses are given in the graphs represented in FIG. 3 for the experiments over a short period, and in FIG. 4 for the experiments over a long period. A C-terminal degradation of rHV2-Lys47 occurs in the plasma, which explains the difference in quantification results obtained by the ELISA test and by the activity test. In fact, one of the two antibodies used for the ELISA test recognises the C-terminal portion of rHV2-Lys47, and therefore no longer recognises the degraded molecules which remained active.

However, it is observed that, for the same quantity of rHV2-Lys47 injected into the rats in free form or in the form of a conjugate with MPEG 5,000, the plasma concentration of MPEG 5,000-rHV2-Lys47 is 7 to 8 times higher than that of free rV2-Lys47. For the same level of inhibition, 7 to 8 times less MPEG 5,000-rHV2Lys47 can therefore be injected than free rHV2-Lys47.

The pharmacokinetic results presented in FIG. 4 confirm that the half-life period of MPEG 5,000-rHV2Lys47 is increased compared to that of rHV2-Lys47. On the other hand, the half-life period of PEG 50,000-rHV2-Lys47 is substantially greater than that for the two above. Indeed, 3 hours after the injection, an anti-thrombin activity greater than 50% can be measured in rats treated with the PEG 50,000-rHV2-Lys47 conjugate and about 30% in rats treated with the MPEG 5,000-rHV2-Lys47 conjugate compared with the activity initially measured before the injection. An anti-thrombin activity of less than 10% is measured 8 hours after injecting rats with hirudin in free form.

The cost of producing the MPEG 5,000-rhV2-Lys47 prepared according to the invention being only slightly increased compared to the cost of production of free rHV2-Lys47, the use of MPEG 5,000-rHV2-Lys47 in pharmacology could be of a substantially reduced cost compared with the use of rHV2-Lys47.

We claim:

1. Process for preparing a polyethylene glycol-hirudin conjugate comprising:
   a) activating polyethylene glycol (PEG) by reaction with carbonyldiimidazole in an anhydrous solvent,
   b) recovering the activated PEG by precipitation with a hydrophobic solvent,
   c) condensing the activated PEG of step b) with hirudin in a slightly alkaline medium, and
   d) purifying the conjugate obtained in step c).

2. Process according to claim 1, wherein the process is carried out in an anhydrous solvent which is a polar aprotic solvent.

3. Process according to claim 1, wherein the anhydrous solvent is selected from the group consisting of dioxane, dimethylformamide, acetonitrile, dimethyl sulphoxide and tetrahydrofuran.

4. Process according to claim 1, wherein the hydrophobic solvent is an apolar or barely polar aprotic solvent.

5. Process according to claim 1, wherein the hydrophobic solvent is an aliphatic ether or an aliphatic hydrocarbon.

6. Process according to claim 1, wherein the hydrophobic solvent is selected from the group consisting of ethyl ether, pentane, hexane and heptane.

7. Process according to claim 6, wherein the hydrophobic solvent is ethyl ether.

8. Process according to claim 1, wherein the molar ratio between carbonyldiimidazole and PEG is between 5 and 50.

9. Process according to claim 8, wherein the molar ratio between carbonyldiimidazole and PEG is between 10 and 20.

10. Process according to claim 1, wherein the conjugate obtained is purified by the following two successive steps:
    a) anion-exchange chromatography to remove unreacted PEG, and
    b) reversed-phase chromatography to separate the conjugate obtained from residual free hirudin.

11. Process according to claim 1, wherein the PEG has a molecular weight of between 2,000 and 100,000, and the PEG is $C_1$–$C_6$ aliphatic monoesters of polyethylene glycol.

12. Conjugate obtained according to the process of claim 1.

13. Polyethylene glycol-hirudin conjugate, wherein polyethylene glycol (PEG) is bound to himdin via at least one amine functional group of hirudin, wherein said at least one amine functional group is not a terminal amine functional group of hirudin.

14. Conjugate according to claim 13, wherein more than 60% by weight of the conjugate have an antithrombotic activity.

15. Conjugate according to claim 13, wherein the PEG has a molecular weight of between 2,000 and 100,000 and the PEG is $C_1$–$C_6$ aliphatic monoesters of polyethylene glycol.

16. Process according to claim 15, wherein the PEG has a molecular weight between 2,000 and 50,000.

17. A method of treating thromboses by administering an effective amount of the conjugate according to claim 13 to a patient in need thereof.

* * * * *